(12) United States Patent
Amador

(10) Patent No.: US 7,309,506 B2
(45) Date of Patent: Dec. 18, 2007

(54) ENZYMATIC METHOD OF PRODUCING A LACTOSE-FREE CALCIUM PRODUCT

(76) Inventor: Luz Maria Amador, 1044 E. Edgemont Dr., Fresno, CA (US) 93720

( * ) Notice: Subject to any disclaimer, the term of this patent is extended or adjusted under 35 U.S.C. 154(b) by 0 days.

(21) Appl. No.: 11/180,141

(22) Filed: Nov. 17, 2005

(65) Prior Publication Data

US 2006/0057253 A1  Mar. 16, 2006

Related U.S. Application Data

(60) Provisional application No. 60/588,303, filed on Jul. 15, 2004.

(51) Int. Cl.
*A23L 1/303* (2006.01)

(52) U.S. Cl. .................. 426/74; 426/580; 426/583; 426/588

(58) Field of Classification Search ............. 426/74, 426/580, 583, 588
See application file for complete search history.

(56) References Cited

U.S. PATENT DOCUMENTS

| | | | | | |
|---|---|---|---|---|---|
| 4,740,380 | A | * | 4/1988 | Melachouris et al. | 426/590 |
| 4,851,243 | A | * | 7/1989 | Andersen et al. | 426/74 |
| 4,853,246 | A | * | 8/1989 | Stevens | 426/580 |
| 5,204,134 | A | * | 4/1993 | Girsh | 426/580 |
| 5,942,264 | A | * | 8/1999 | Monte | 426/42 |

* cited by examiner

*Primary Examiner*—Helen Pratt

(57) ABSTRACT

An enzymatic method to extract lactose-free calcium from dairy whey and milk with the steps of: adding an enzyme (yeast lactase or any other named related lactose reducing enzyme) to the whey permeate in order to precipitate the lactose. The pH should be maintained below 7.2 and temperature below 172 F. The system is cooled down and the product is pumped to a tank equipped with an agitator to agitate the product and promote the hydrolysis. The slurry is pumped for further drying. The optimum temperature for the process using lactase is 90° F. to 122° F. After the enzyme is added to the liquid, the tanks are agitated for not least of 8 hours previous to the drying process.

1 Claim, 1 Drawing Sheet

US 7,309,506 B2

ENZYMATIC METHOD OF PRODUCING A LACTOSE-FREE CALCIUM PRODUCT

CROSS REFERENCE TO RELATED APPLICATIONS

This is a continuation in part of Ser. No. 60/588,303, filed on Jul. 15, 2004.

STATEMENT REGARDING FEDERALLY SPONSORED RESEARCH OR DEVELOPMENT

Not Applicable

DESCRIPTION OF ATTACHED APPENDIX

Insert Description of Attached Appendix Here.

BACKGROUND OF THE INVENTION

This invention relates generally to the field of and more specifically to an enzymatic method to extract Lactose-free calcium and related minerals or protein from dairy whey and milk.

During the past years there have been numerous studies that highlight the benefits of adequate Calcium intake to prevent some conditions and diseases such as overweight, diabetes, certain types of cancers and cardiovascular problems. There has been a global increase of milk calcium production to satisfy the requirements created by the introduction of food supplements. After a search for a commercial product contacting large manufacturers of Milk calcium, I discovered that there was no commercial lactose-free commercial product.

After learning about the need and in reviewing the statistical numbers of a growing population in need for such product I designed the enclosed method to eliminate the lactose.

At the same time I knew of the preferences to obtain a product with a higher concentration of calcium for pharmaceutical use and the requirements for whiter finished product.

Previous process rendered 24-27% Calcium in the final product. The novel enzymatic method, which I introduced, increases substantially the yield of Calcium and provides a product with typical Calcium concentration between 28-32%, depending of the moisture conditions that the equipment could control.

Calcium is a mineral that the body needs for numerous functions, including building and maintaining bones and teeth, blood clotting, the transmission of nerve impulses, and the regulation of the heart's rhythm. Ninety-nine percent of the calcium in the human body is stored in the bones and teeth. The remaining 1 percent is found in the blood and other tissues.

To ensure that 95 percent of the population gets this much calcium, the National Academy of Sciences established the following recommended intake levels:

1,000 mg/day for that age 19-50
1,200 mg/day for that age 50 or over
1,000 mg/day for pregnant or lactating adult women To have an adequate intake of calcium and other minerals it is recommended the consumption of milk, but unfortunately there is large number of individuals that are lactose intolerant so the main goal of this invention is to introduce a manufacturing method to eliminate lactose in the calcium in order to have a product suitable for lactose intolerant individuals as well as for diabetic and non-diabetic individuals. Consumption of calcium and dairy products has benefits beyond bone health, including possibly lowering the risk of high blood pressure and colon cancer. While the blood pressure benefits appear fairly small, the protection against colon cancer seems somewhat larger. In addition high levels of galactose, a sugar released by the digestion of lactose in milk, have been studied as possibly damaging to the ovaries and leading to ovarian cancer. Although such associations have not been reported in all studies, there may be potential harm in consuming high amounts of dairy products.

Lactose Intolerance

Millions of people have some degree of lactose intolerance. For them, eating or drinking dairy products causes problems like cramping, bloating, gas, and diarrhea. These symptoms can range from mild to severe. Certain groups are much more likely to have lactose intolerance. For example, 90 percent of Asians, 70 percent of blacks and Native Americans, and 50 percent of Hispanics are lactose-intolerant, compared to only about 15 percent of people of North America.

Existing process to obtain milk calcium does not eliminate the lactose and there is no history of previous attempt to use an enzymatic process.

Direct communication with one of the leaders of the industry (Glanbia) confirmed this fact.

Prior technology didn't allow for removal of lactose. The present process eliminates the lactose in the final product, making the product available for the millions of individuals that are lactose intolerant.

Prior technology created drying problems due to the existence of sugars in the product to be dried. The present technology reduces the use of energy and makes the drying process more efficient.

The product obtained is whiter and the sweet flavor is also eliminated, creating a product that could be use in a wider variety of consumer products.

The particle size for the product becomes more homogeneous.

The elimination of the sugars promotes a larger shelf life for the product.

The product becomes more stable since there increase in effectiveness from drying reduces the moisture in the final product.

The previous product was highly hygroscopic. Since the sugars are eliminated the resulting product obtained using this process elongates the shelf life of the product.

BRIEF SUMMARY OF THE INVENTION

The primary object of the invention is a lactose free product obtained from milk. The resulting product would satisfy the need from pharmaceutical, nutraceutical and food requirements to provide a high quality source of calcium phosphate.

Another object of the invention is higher total percentage of Calcium in the final product.

Another object of the invention is higher recovery of solids in the process.

A further object of the invention is Creation of a Nobel method to increase energy efficiency. This process reduces the amount of energy used to dry product.

Yet another object of the invention is to increase the quality of total solids profile. Previous process provided higher percentage of large particles (30 microns). The use of this method produces a product with higher percentage of particles below 30 microns.

Still yet another object of the invention is for certain pharmaceutical, nutraceutical and food uses the final product used to be milled. Because of the change in particle size distribution is modified there will be not additional need to mill the product for certain uses.

Another object of the invention is to eliminate the need to keep the product under refrigeration conditions. The traditional process to obtain this product was a batch system that required maintenance of the product at or below 45° F. Because the process eliminates the sugars in the system the product is not longer in need of refrigeration. There are substantial savings as the product could be maintained in the tanks previous to drying at ambient temperature eliminating the refrigeration costs.

Another object of the invention is that the product obtained is whiter, which in many cases is a requirement for some industries such is the case of the pharmaceutical industry.

A further object of the invention is that the product obtained eliminates the sweet flavor, allowing for use in a wider range of products without altering their original organoleptic characteristics.

Other objects and advantages of the present invention will become apparent from the following descriptions, taken in connection with the accompanying drawings, wherein, by way of illustration and example, an embodiment of the present invention is disclosed.

In accordance with a preferred embodiment of the invention, there is disclosed an enzymatic method to extract Lactose-free calcium from dairy whey and milk comprising the steps of:

1) Adding an enzyme (yeast Lactase or any other named related lactose reducing enzyme) to the whey permeate in order to precipitate the lactose. The pH should be maintained below 7.2 and temperature below 172° F.
2) The enzyme catalyzes the glucose and galactose from lactose. The lactase hydrolyzes lactose's beta D-galactosides linkages yielding one mole of D-glucose and one mole of D-galactose
3) The system is cooled down and the product is pumped to a tank equipped with an agitator to agitate the product and promote the hydrolysis.
4) The slurry is pumped for further drying.

DETAILED DESCRIPTION OF THE PREFERRED EMBODIMENTS

Figure 1:
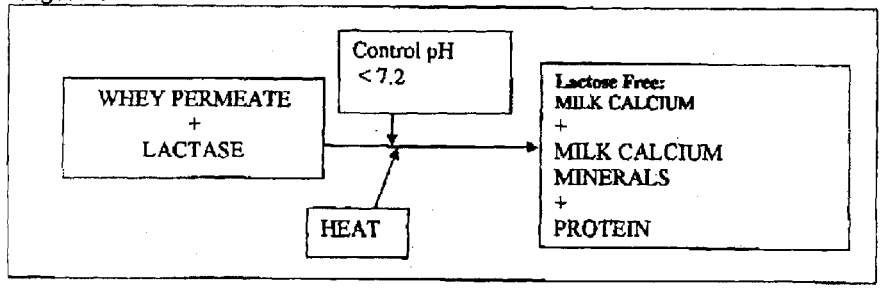
FIG. 1 A flow chart of the operations that comprise the method.
Figure 2:
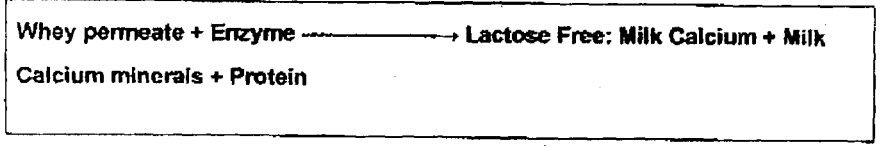
FIG. 2 Addition of Enzyme.

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

The main advantage of a lactose-free product obtained from milk whey or any other related source of animal milk is that it provides a source of calcium phosphate that is readily available for human nutrition and is adequate for lactose intolerant individuals. However there are other advantages such as the creation of a novel method to obtain Milk Calcium of higher quality (higher percentage of Calcium) and the introduction of an enzymatic method that drastically diminishes the consumption of energy during the drying process.

This new method allows for the creating of a higher quality product since the product obtained is
a) Whiter.
b) Less expensive due to savings in energy and drying time.
c) No sweetens of final product, allowing for a wider use of the product.
d) More stable, since the moisture is lower in the final product and increases the shelf life
e) Easier to control microbiological parameters.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

I claim:

1. A method of producing a calcium containing lactose-free milk product comprising treating a milk product from the group consisting of whey from milk, waste from animal milk, and any other milk product comprising treating the milk product with a lactase enzyme at a temperature under 170 F., and a pH of under 7.2 to make a lactose-free composition, separating the fluid from the composition, drying said composition, and grinding the milk composition; or drying the milk composition after fluid separation, and then grinding the lactose free milk-calcium containing composition, wherein the lactose-free composition contains milk calcium, milk minerals and milk protein.

* * * * *